US007720542B2

(12) United States Patent
Jolly

(10) Patent No.: US 7,720,542 B2
(45) Date of Patent: May 18, 2010

(54) REMOTE SENSING AND ACTUATION OF FLUID IN CRANIAL IMPLANTS

(75) Inventor: Claude Jolly, Innsbruck (AT)

(73) Assignee: MED-EL Elektromedizinische Geraete GmbH, Innsbruck (AU)

(*) Notice: Subject to any disclaimer, the term of this patent is extended or adjusted under 35 U.S.C. 154(b) by 0 days.

(21) Appl. No.: 11/854,708

(22) Filed: Sep. 13, 2007

(65) Prior Publication Data
US 2008/0039771 A1 Feb. 14, 2008

Related U.S. Application Data

(63) Continuation-in-part of application No. 11/778,165, filed on Jul. 16, 2007.

(60) Provisional application No. 60/831,351, filed on Jul. 17, 2006.

(51) Int. Cl.
*A61N 1/00* (2006.01)
*A61K 9/22* (2006.01)
(52) U.S. Cl. .............. 607/55; 604/890.1
(58) Field of Classification Search .......... 604/890.1, 604/891.1; 623/10; 607/55–57, 137
See application file for complete search history.

(56) References Cited

U.S. PATENT DOCUMENTS 5,411,467 A * 5/1995 Hortmann et al. .......... 600/25

| 6,259,951 | B1 * | 7/2001 | Kuzma et al. ........... 607/57 |
| 6,629,911 | B2 | 10/2003 | Puria et al. .......... 600/25 |
| 2003/0097121 | A1 * | 5/2003 | Jolly et al. .......... 604/891.1 |
| 2005/0177204 | A1 | 8/2005 | Zhang et al. |

FOREIGN PATENT DOCUMENTS

| DE | 391806 C1 | 9/1990 |
| DE | 3918086 C1 | 9/1990 |
| WO | WO03/034960 | 5/2003 |
| WO | WO2004/024212 | 3/2004 |

OTHER PUBLICATIONS

International Search Report dated Aug. 4, 2009, 5 pages.
International Search Report ; PCT/US2007/073572.

* cited by examiner

*Primary Examiner*—Kevin C Sirmons
*Assistant Examiner*—Elizabeth R Moulton
(74) *Attorney, Agent, or Firm*—Sunstein Kann Murphy & Timbers LLP

(57) ABSTRACT

An implantable device is described. An implantable transducer converts between electrical energy and acoustic energy. An implantable electronics module is in communication with the transducer and processes electronic data signals associated with the transducer. A fluid filled catheter has a proximal end coupled to the transducer, and a distal end having a distal opening to cerebrospinal fluid in an implanted patient.

21 Claims, 5 Drawing Sheets

REMOTE SENSING AND ACTUATION OF FLUID IN CRANIAL IMPLANTS

This application is a continuation-in-part of U.S. application Ser. No. 11/778,165, filed Jul. 16, 2007, which in turn claims priority from U.S. Provisional Patent Application 60/831,351, filed Jul. 17, 2006, the contents of which are incorporated herein by reference.

FIELD OF THE INVENTION

The present invention relates to implantable devices, and more particularly to implantable devices for mechanical and electrical stimulation and fluid delivery to the brain.

BACKGROUND ART

The following discussion of implantable devices uses the specific example of the auditory system and cochlear implants. But the present invention is not limited to that specific application and is extensible to other implantable systems and devices, including without limitation brain-related functioning and corresponding cranial implants.

FIG. 1 shows the anatomy of a normal human ear. A normal ear transmits sounds through the outer ear 101 to the eardrum 102, which moves the three bones of the middle ear 103, which in turn excites the cochlea 104. The cochlea, or inner ear, 104 includes an upper channel known as the scala vestibuli 105 and a lower channel known as the scala tympani 106, which are connected by the cochlear duct 107. In response to received sounds, the stapes, a bone of the middle ear 103, transmits vibrations via the fenestra ovalis, (oval window) 114, to the perilymph (cerebrospinal fluid) of the cochlea 104. Vibrations in the cerebrospinal fluid are dissipated out of the fenestra rotunda (round window) 115. As a result, the hair cells of the organ of Corti are excited to initiate chemical-electric pulses that are transmitted to the cochlear nerve 113, and ultimately to the brain.

Some patients may have partially or completely impaired hearing for reasons including: long term exposure to environmental noise, congenital defects, damage due to disease or illness, use of certain medications such as aminoglycosides, or physical trauma. Hearing impairment may be of the conductive, sensory neural, or combination types.

There are several types of middle- and inner-ear implants that can restore a sense of partial or full hearing. Implants often include various electromagnetic transducers that may function as an actuator, a sensor, and/or a switch. An example of an implant with an electromagnetic actuator is a middle ear implant which mechanically drives the ossicular chain, the three bones of the middle ear that mechanically connect the eardrum to the oval window. Another example of an implant with an electromagnetic actuator is a middle ear implant that mechanically drives the tympanic membrane.

Another type of implant relies on direct electrical stimulation of the nerves in the inner ear. For example, intra-cochlear electrodes can restore some sense of hearing by direct electrical stimulation of the neural tissue in proximity of an electrode contact. These electrodes are typically located on the end of an electrode carrier that is threaded into the cochlea. The electrodes are connected to, for example, an implanted signal processor which communicates with an external signal processor that produces an electrical stimulation signal for the implanted electrodes to stimulate the cochlear nerve.

In order to treat certain inner ear disorders, it is often necessary to deliver therapeutic agents directly into the cochlea. An example of a system for delivering therapeutic agents to the inner ear is a catheter that is inserted into the cochlea via the round window. The end of the catheter might be infused with a therapeutic agent that is released into the cerebrospinal fluid. The catheter might also include a fluid reservoir with a solution of the therapeutic agent that is in fluid communication with the cerebrospinal fluid. Alternatively, the catheter might include a fluid filled lumen containing a solution of the therapeutic agent that is in fluid communication with the cerebrospinal fluid. Delivery of therapeutic agents to the cochlea is described further in U.S. patent application Ser. No. 11/374,505, filed Mar. 13, 2006, the contents of which are incorporated herein by reference.

SUMMARY OF THE INVENTION

In an embodiment of the present invention, an implantable device includes an implantable transducer that converts between electrical energy and acoustic energy. An implantable electronics module is in communication with the transducer and processes electronic data signals associated with the transducer. A fluid filled catheter has a proximal end coupled to the transducer, and a distal end having a distal opening to cerebrospinal fluid in an implanted patient.

In a further specific embodiment, a housing chamber contains housing fluid in communication with the fluid in the proximal end of the catheter. The housing chamber may further contain the transducer, or the transducer may be outside the housing chamber. There may be a fluid port in the housing chamber for receiving therapeutic fluid for delivery via the catheter to the brain. A microphone may be in communications with the housing fluid and the electronics module for sensing acoustic signals at the proximal end of the catheter representing acoustic activity near the distal end of the catheter. The transducer may specifically be a floating mass transducer and/or may be adapted to be secured to the skull of the implanted patient.

Embodiments also include an implantable device having an implantable transducer for converting between electrical energy and acoustic energy. An implantable electronics module is in communication with the transducer and processes electronic data signals associated with the transducer to produce an electrical stimulation signal. An electrode stimulator is coupled to the electronics module for stimulating neural tissue of the brain with the stimulation signal. A fluid filled catheter has a proximal end coupled to the transducer, and a distal end having a distal opening to cerebrospinal fluid in an implanted patient.

In a further such specific embodiment, the distal end of the catheter is located on the electrode stimulator. The catheter may be contained within the electrode stimulator, or located outside the electrode stimulator.

In a further specific embodiment, a housing chamber contains housing fluid in communication with the fluid in the proximal end of the catheter. The housing chamber may further contain the transducer, or the transducer may be outside the housing chamber. There may be a fluid port in the housing chamber for receiving therapeutic fluid for delivery via the catheter to the brain. A microphone may be in communications with the housing fluid and the electronics module for sensing acoustic signals at the proximal end of the catheter representing acoustic activity near the distal end of the catheter. The transducer may specifically be a floating mass transducer and/or may be adapted to be secured to the skull of the implanted patient.

DETAILED DESCRIPTION OF SPECIFIC EMBODIMENTS

In the past, cranial sensing devices and amplifiers have been brought into the closest feasible proximity to the structures of the brain. But this approach has many problems and is difficult to implement in practice. Embodiments of the present invention dispose the device at structures within the user having more spacious and accessible locations not directly adjacent to the sensing location by using a catheter to establish fluid communication between the sensing location and the system devices. The catheter can be filled with a vibration transmitting liquid, for example, by a port and/or septum membrane. The distal end of the catheter terminates at some cranial location and the proximal end couples to an implantable transducer. Enclosing the fluid within the catheter isolates it from the cerebrospinal fluid to avoid leaks and prevent bacterial contamination while providing convenient mechanical access to the brain locations. The catheter may include a semi-permeable membrane at the distal end to provide pharmacological access by use of therapeutic drugs adapted to migrate across the membrane into the cerebrospinal fluid. In some embodiments, the proximal end of the catheter may also be coupled to a self-sealing semi-permeable septum membrane that allows the therapeutic drugs to be introduced in the catheter fluid. For example, the proximal end membrane may be located in the middle ear or mastoid cavity for actuation or sensing of the catheter fluid. In some embodiments, the membranes may also usefully be coupled to a microphone which senses the fluid mechanics associated with cranial structures. Thus, embodiments of the present invention provide a safe and convenient leak proof and bacterial resistant interface between an implanted prosthetic system and the cerebrospinal fluid.

Figure 1:
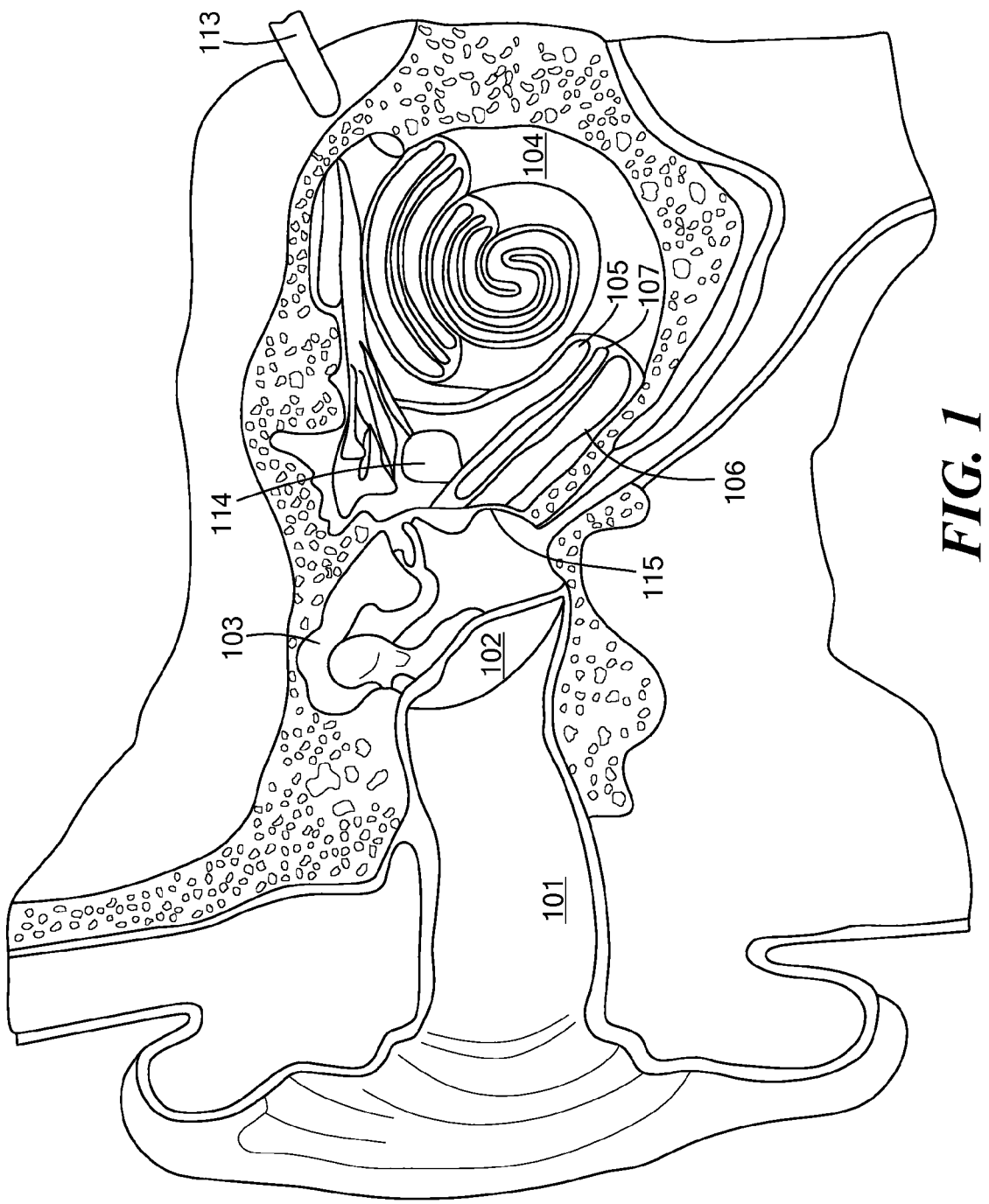
FIG. 1 shows the structure of the normal human ear.
Figure 2B:
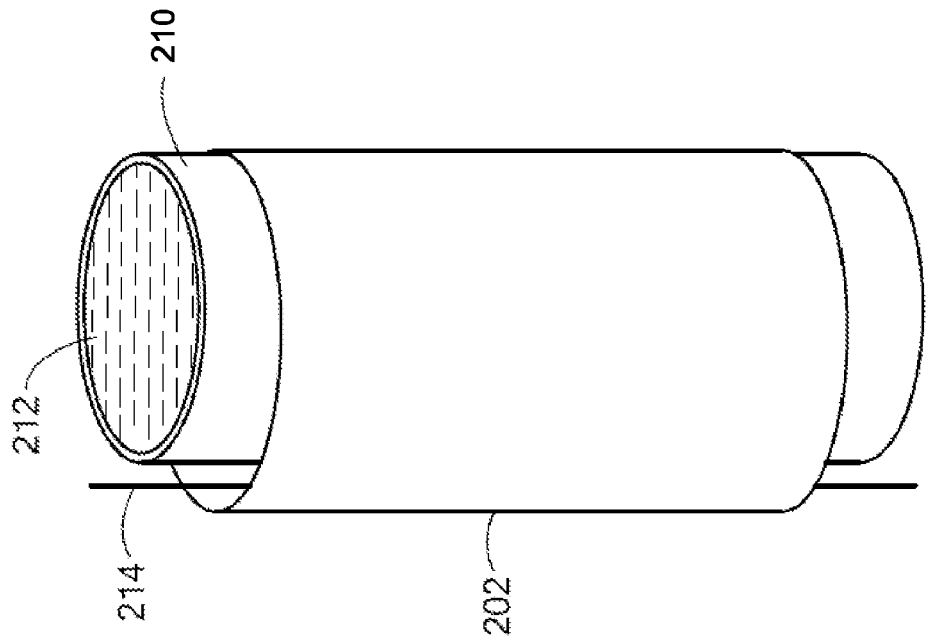
FIG. 2B is a cut-away illustration of a catheter of the present invention.
Figure 2A:
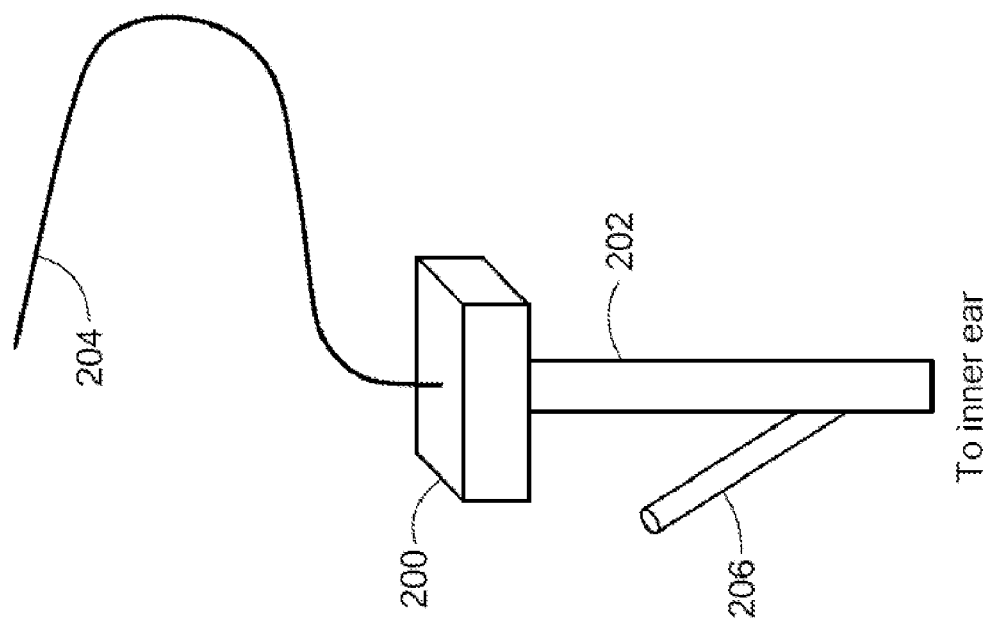
FIG. 2A is a graphical illustration of an embodiment of the present invention.

FIG. 2A is a graphical illustration of one embodiment of the invention showing a transducer-catheter arrangement. FIG. 2B is a cut-away cross-section of a portion of a cranial catheter. In this embodiment, an implantable transducer 200 is connected to the proximal end of a cranial catheter 202. Wiring 204 may connect the implantable transducer 200 to external circuitry. A fluid port 206 provides access to a catheter lumen 210 within the cranial catheter 202. Cranial catheter 202 can also include an electrode wire 214 that runs along the length of the catheter. Implantable transducer 200 converts electrical energy into mechanical vibrations, and vice versa. For example, implantable transducer 200 may produce vibrations in the human auditory range. Catheter lumen 210 is filled with a catheter fluid 212 (for example via septum port 206), which can transmit vibrations that are generated by the implantable transducer 200 to the fluid of the inner ear. The implantable transducer 200 is connected to the proximal end of the cranial catheter 202 such that vibrations generated by the implantable transducer 200 are transmitted into the catheter fluid 212. There is cooperation between the implantable transducer 200, catheter lumen 210, and catheter fluid 212 such that a sufficient and appropriate amount of mechanical energy is generated by the implantable transducer 200 and is transmitted by the catheter fluid 212 to the distal end of the catheter. Alternatively, fluid movement generated near the proximal end of the catheter may be transmitted through the catheter fluid 212 and detected by a sensitive membrane (e.g., a microphone diaphragm) associated with the implantable transducer 200.

For example, the distal end of the cranial catheter 202 may be placed at or near the surface of the dura mater. This may be accomplished, for example, by drilling a small hole through the cortical bone until the dura mater is just accessible. Once the distal end opening of the cranial catheter 202 is adjacent to the dura, fluid vibration originating from the implantable transducer 200 can be transmitted all the way to the cochlea through the cerebrospinal fluid, even though some attenuation will take place due to the membrane layers around the brain. Still such an approach does not require a mastoidectomy, and the procedure may be done on an outpatient basis using local anesthesia.

The catheter fluid 212 may be an artificial perilymph, or a physiological saline when the catheter lumen 210 is open to the cerebrospinal fluid. If the distal end of the cranial catheter 202 is to be placed in the scala media, then the catheter fluid 212 may usefully be an artificial endolymph. The catheter fluid 212 may be any liquid that facilitates or emphasizes mechanical energy transmission. The cranial catheter 202 may be at least partially in the form of a channel through an implant electrode. Or the cranial catheter 202 may be a separate catheter in parallel with an implant electrode. The cranial catheter 202 may be made of an incompressible material to optimize transmission through the fluid 212 with minimal loss of energy. The volume of the catheter fluid 212 may usefully be minimized in order to maximize transmission of mechanical movements in the catheter fluid between the distal and proximal ends of the cranial catheter 202.

The catheter lumen 210 may be open ended to the cerebrospinal fluid, or it may be at least partially closed by a sensitive membrane such as a bacterial filter. The membrane may also prevent protein transport from the cerebrospinal fluid through the catheter lumen 210, and inhibit other diffusion processes. The membrane may be self-sealing and/or semi-porous to allow semi-permeable access to therapeutic drugs.

Figure 3:
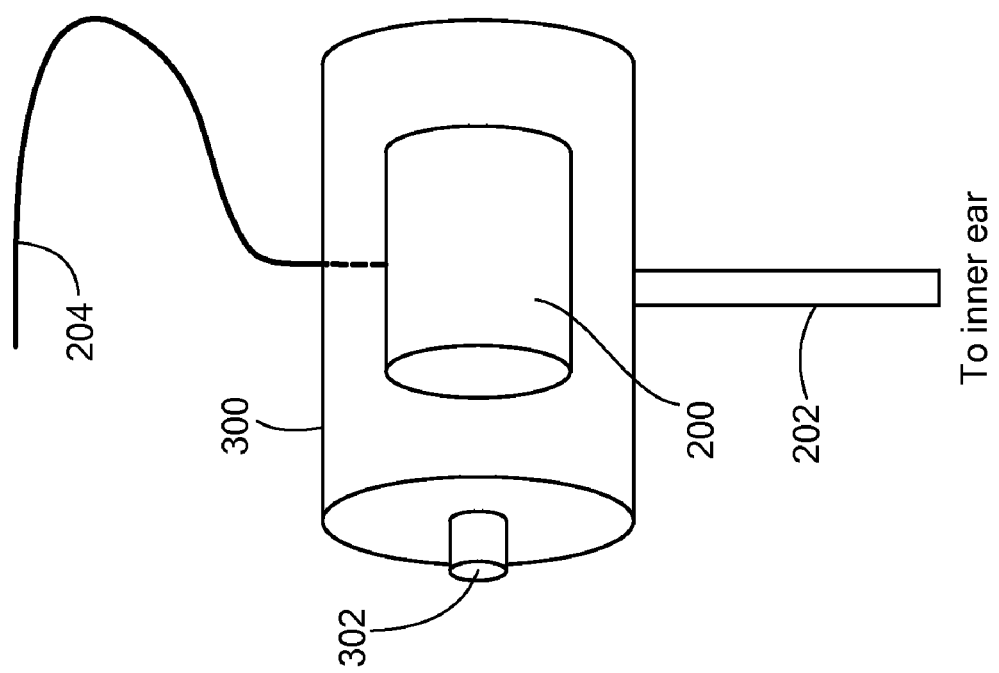
FIG. 3 is a graphical illustration showing a transducer enclosed in a housing chamber.

FIG. 3 shows another transducer arrangement in which implantable transducer 200 is inside a housing chamber 300 that is filled with a fluid, and disposed such that vibrations generated by transducer 200 are transmitted to the chamber fluid. A septum port 302 with septum can be used for access to the fluid in housing chamber 300. The septum port 302 allows the housing chamber 300 and cranial catheter 202 to be filled with a liquid of chosen composition. One challenge is to be able to fill the cranial catheter 202 with a catheter liquid for optimal coupling between the implantable transducer 200 and the fluid of the inner ear, and also providing an effective seal between the middle ear and the inner ear. Cranial catheter 202 connects to housing chamber 300 so that mechanical vibrations generated by the implantable transducer 200 will be transmitted through the chamber fluid to the catheter fluid 212. The fluid in the housing chamber 300 may be in fluid communication with the catheter fluid 212. Vibrations generated by the implantable transducer 200 are transmitted through the catheter fluid 212 to the cerebrospinal fluid. In this arrangement, the implantable transducer 200 may be, for example, a floating mass transducer such as a vibrant FMT.

Figure 4:
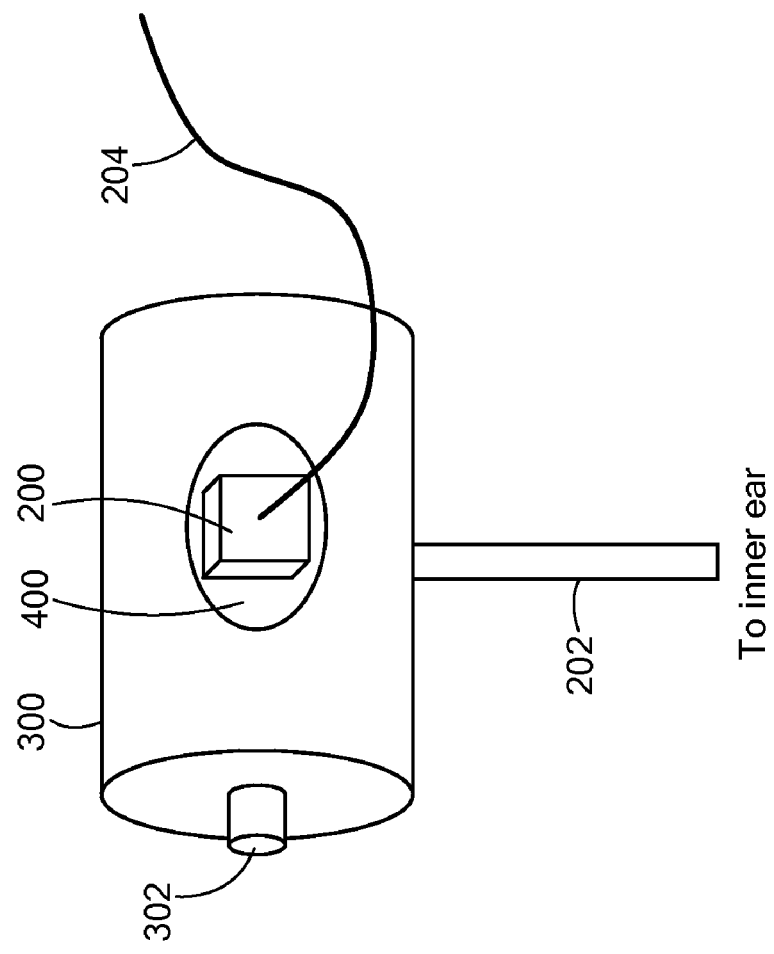
FIG. 4 is a graphical illustration showing a housing chamber having an external membrane, with the transducer in contact with the membrane.

FIG. 4 shows another transducer arrangement also involving a housing chamber 300. As in the embodiment of FIG. 3, cranial catheter 202 connects to the housing chamber 300 so that mechanical vibrations will be transmitted through the chamber fluid to the catheter fluid 212. A septum port 302 can be used to fill the cranial catheter 202 with the catheter fluid 212 and to provide access to the fluid in the housing chamber 300 through the port septum 302 The fluid in housing chamber 300 may be in fluid communication with the catheter fluid 212. In this embodiment, housing chamber 300 includes a housing membrane 400 through which vibrations can be transmitted to the chamber fluid (FIG. 4). Implantable transducer 200 is external to the housing chamber 300, and is arranged and mounted with respect to the housing membrane 400 so that mechanical vibrations generated by the implantable transducer 200 will be transmitted through the housing membrane 400 via the chamber fluid to the catheter fluid 212. These vibrations are then transmitted via the catheter fluid 212 through the distal end of the catheter to the cerebrospinal fluid.

Figure 5:
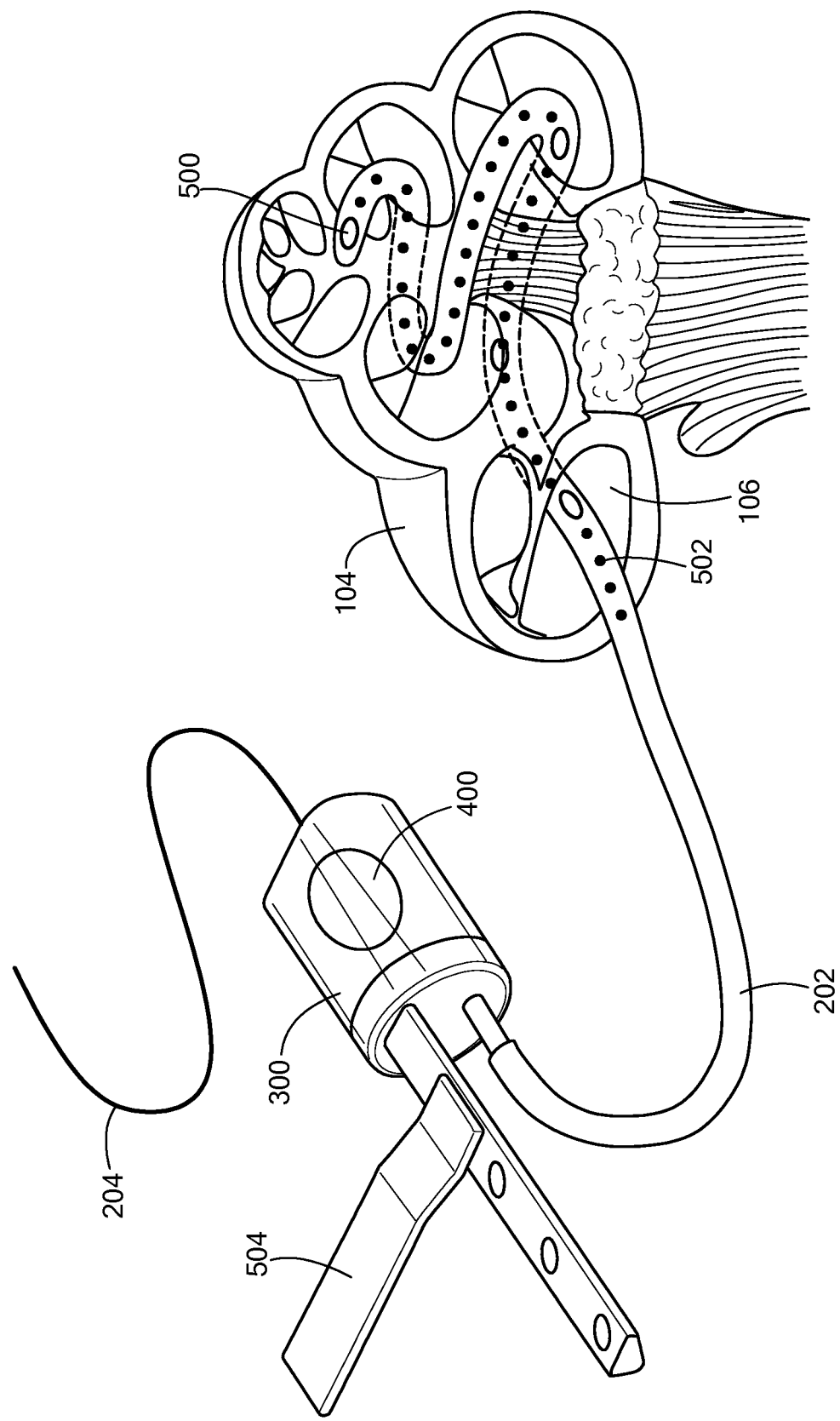
FIG. 5 is a pictorial illustration of an embodiment of the present invention showing a catheter threaded into the cochlea.

FIG. 5 is a pictorial illustration of a general embodiment of the present invention showing the cranial catheter threaded into the cochlea 104 of a patient user. In this embodiment, the implantable transducer 200 can be situated inside the housing chamber 300 as in the embodiment of FIG. 3. The implantable transducer 200 can also be external to the housing chamber 300 and mounted against the housing membrane 400 as in the embodiment of FIG. 4. The housing membrane 400 can also be used, for example, to monitor the output of the implantable transducer 200 when it is situated inside the housing chamber 300. The housing membrane 400 can also be of a selectively porous material such that therapeutic agents may be introduced into the housing fluid for delivery via the catheter fluid 212 to the inner ear. A mounting bracket 504 is shown that can be used to mount the implantable transducer 200 to another assembly, or, in another configuration, directly to the bone (such as the skull) or other structures in the ear. In the embodiment shown, the cranial catheter 202 also includes catheter membranes 500 and an electrode array 502. The catheter membranes 500 transmit the vibrations of the implantable transducer 200 from the catheter fluid 212 to the cerebrospinal fluid. In other embodiments, the catheter membranes 500 might be open ports or selectively porous membranes that allow therapeutic agents within the catheter fluid 212 to be delivered to the cerebrospinal fluid. The electrode array 502 is connected to an electrode wire 214 and is used for electrical stimulation of the neural tissue of the inner ear. In such an arrangement, the electrode wire 214 may be connected to an implanted audio processor under the skin of a user near the outer ear.

Figure 6:
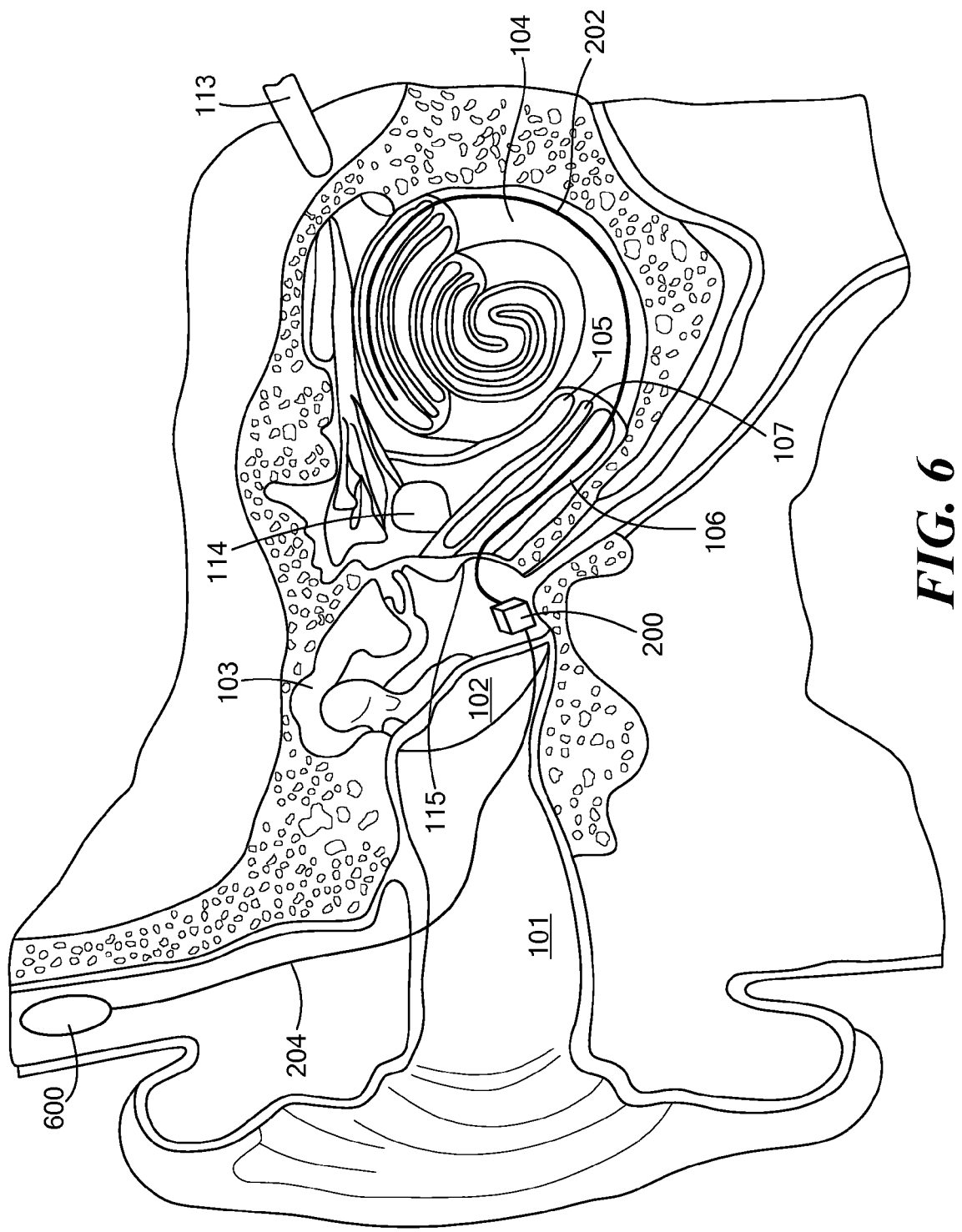
FIG. 6 shows the structure of the normal human ear with an embodiment of the present invention implanted in the cochlea.

FIG. 6 shows the structure of an ear along with an embodiment of the present invention implanted in the cochlea. The cranial catheter 202 is threaded into the scala tympani 106 of the cochlea 104 via the round window 115. The implantable transducer 200 is shown within the middle ear. Wiring 204 can be used to connect the implantable transducer 200 and the electrode array 502 to other circuitry. For example, the electrode array 502 may be connected via the wiring 204 to an implanted audio processor 600 located under the skin near the outer ear. An audio processor 600 receives an audio signal and produces an electrical stimulation signal that is transmitted to the electrode array 502 via the wiring 204 for electrical stimulation of the neural tissue of the inner ear. The audio processor 600 contains electronic components for accepting an audio input from an audio source. In various embodiments, the audio processor 600 will accept analog signals, digital signals, or both. The audio input may be, but is not limited to, an analog or digital output from a microphone, telephone, television, stereo system, mp3 player, radio receiver, or computer. The audio input may be accepted via wired or wireless connection.

While the inventive system has been particularly shown and described, it is not intended to be exhaustive nor to limit the invention to the embodiments disclosed. It will be apparent to those skilled in the art that modifications can be made to the present invention without departing from the scope and spirit thereof. For example, while the embodiments shown have generally described a system to transmit vibrations produced by a transducer to the inner ear, the transducer can also be used to detect vibrations in the cerebrospinal fluid via the catheter fluid. While the embodiments shown include wire for connecting various components, the wire is optional. This connection may be wireless, or the components may be optional. It is intended that the scope of the invention be defined by the claims appended hereto and their equivalents.

What is claimed is:

1. An implantable device for implanting in a patient comprising:
    an implantable transducer for converting between electrical energy and acoustic energy;
    an implantable electronics module, in communication with the transducer, for processing electronic data signals associated with the transducer; and
    a catheter having a proximal end and a distal end, the proximal end being coupled to the transducer such that vibrations may be transmitted from the transducer to fluid within the catheter, and the distal end having a distal opening in fluid communication with the proximal end, the catheter permitting fluid delivery of the fluid within the catheter from the proximal end to the distal end and through the distal opening to cerebrospinal fluid of the patient.

2. An implantable device according to claim 1, further comprising:
    a housing chamber for containing housing fluid, the housing chamber in fluid communication with the proximal end of the catheter.

3. An implantable device according to claim 2, wherein the housing chamber further contains the transducer.

4. An implantable device according to claim 2, wherein the transducer is outside the housing chamber.

5. An implantable device according to claim 2, further comprising:
    a fluid port in the housing chamber for receiving therapeutic fluid for delivery via the catheter to the brain.

6. An implantable device according to claim 2, further comprising:
    a microphone, in fluid communication with the housing chamber and the electronics module, for sensing acoustic signals at the proximal end of the catheter representing acoustic activity near the distal end of the catheter.

7. An implantable device according to claim 1, wherein the transducer is a floating mass transducer.

8. An implantable device according to claim 1, wherein the transducer is adapted to be secured to the skull of the patient.

9. An implantable device according to claim 1, wherein the implantable electronics module produces an electrical stimulation signal, the device further comprising:

an electrode stimulator, coupled to the electronics module, for stimulating neural tissue of the brain with the stimulation signal.

10. An implantable device according to claim 9, wherein the distal end of the catheter is located on the electrode stimulator.

11. An implantable device according to claim 9, wherein the catheter is contained within the electrode stimulator.

12. An implantable device according to claim 9, wherein the catheter is located outside the electrode stimulator.

13. An implantable device according to claim 9, further comprising:
    a housing chamber for containing housing fluid, the housing chamber in fluid communication with the proximal end of the catheter.

14. An implantable device according to claim 13, wherein the housing chamber further contains the transducer.

15. An implantable device according to claim 13, wherein the transducer is outside the housing chamber.

16. An implantable device according to claim 13, further comprising:
    a fluid port in the housing chamber for receiving therapeutic fluid for delivery via the catheter to the brain.

17. An implantable device according to claim 13, further comprising:
    a microphone, in communication with the housing fluid and the electronics module, for sensing acoustic signals at the proximal end of the catheter representing acoustic activity near the distal end of the catheter.

18. An implantable device according to claim 9, wherein the transducer is a floating mass transducer.

19. An implantable device according to claim 9, wherein the transducer is adapted to be secured to the skull of the patient.

20. An implantable device according to claim 1, wherein the proximal end of the catheter includes a semi-permeable membrane that permits therapeutic fluid to be introduced into the catheter.

21. An implantable device according to claim 1, wherein the distal end of the catheter includes a semi-permeable membrane that permits therapeutic fluid to migrate across the membrane into the cerebrospinal fluid.

* * * * *